United States Patent [19]

Varma et al.

[11] 4,323,511

[45] Apr. 6, 1982

[54] STEROID DERIVATIVES AND THEIR USE IN RADIOIMMUNOASSAYS

[75] Inventors: Ravi K. Varma, Belle Mead; Sam T. Chao, East Windsor, both of N.J.

[73] Assignee: E. R. Squibb & Sons, Inc., Princeton, N.J.

[21] Appl. No.: 908,294

[22] Filed: May 22, 1978

[51] Int. Cl.$^3$ .............................................. C07J 7/00
[52] U.S. Cl. ........................... 260/397.45; 260/397.4; 260/397.47; 260/397.3; 260/239.55 D; 23/920
[58] Field of Search .......................... 260/397.45, 397.4

[56] References Cited

PUBLICATIONS

Smith et al., J.A.C.S., vol. 72, (1954) p. 1877.
Smith et al., J. Org. Chem., vol. 26, (1961) p. 3856.

*Primary Examiner*—Elbert L. Roberts
*Attorney, Agent, or Firm*—Lawrence S. Levinson; Donald J. Barrack

[57] ABSTRACT

Radiolabeled steroid derivatives having the formula

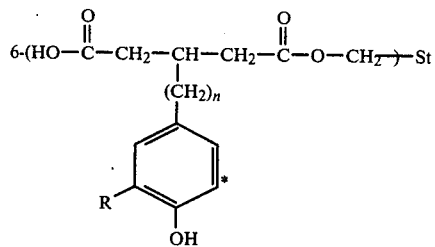

wherein St is a 6-dehydro derivative of a 3-oxo-4,5-dehydro steroid intended for radioimmunoassay, said steroid being saturated in the 1,2-position; R is hydrogen or alkyl of 1 to 3 carbon atoms; n is 0, 1, 2, 3 or 4; and the asterisk (*) indicates tagging with a radioisotope, are useful as tracers in radioimmunoassays. The unlabeled analogs can be coupled with an immunogenic carrier and used to induce antibody formation in animals.

12 Claims, No Drawings

STEROID DERIVATIVES AND THEIR USE IN RADIOIMMUNOASSAYS

RELATED APPLICATION

U.S. patent application Ser. No. 901,952, filed May 1, 1978, discloses steroid derivatives having the formula

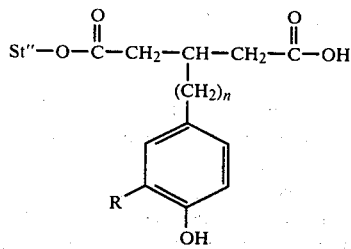

wherein St'' is a des-hydroxy steroid moiety of (i) a hydroxy steroid intended for radioimmunoassay or (ii) a hydroxy containing derivative of a steroid intended for radioimmunoassay, said derivative having a strong affinity for the antibodies of the steroid intended for radioimmunoassay; R is hydrogen or alkyl of 1 to 3 carbon atoms; and n is 0, 1, 2, 3 or 4. It is disclosed that these steroids can be radiolabeled. The application also discloses the anhydrides (formula IV, infra.) used to prepare the steroid derivatives of the instant application.

BACKGROUND OF THE INVENTION

The measurement of various substances by the use of radioimmunoassay techniques has achieved widespread acceptance in recent years. Yalow and Berson, *In Vitro Procedures With Radioisotopes In Medicine,* International Atomic Energy Agency, Vienna (1970), pgs. 455 et seq., express the principle of radioimmunoassay in the following terms:

"Unlabeled antigen in unknown samples competes against labeled antigen ("tracer") for binding to antibody and thereby diminishes the binding of labeled antigen. The degree of competitive inhibition observed in unknown samples is compared with that obtained in known standard solutions for determination of concentration of anitgen in unknowns."

Radioimmunoassay tests require a specific antibody, a radioisotope-labeled (hereinafter referred to as "radiolabeled") antigen, a pure sample of the antigen to be measured to serve as a reference standard, and means for the separation of free antigen from antibody-bound antigen. Radioimmunoassays follow the basic principle of saturation analysis, i.e., competition between labeled and unlabeled antigen for a fixed number of antibody binding sites.

When radiolabeled antigen, unlabeled antigen, and antibody are brought together, the amount of radiolabeled antigen bound to antibody and the amount of radiolabeled antigen remaining unbound (free) has a direct relationship to the amount of unlabeled antigen present when a given amount of antibody is present. Thus, by using a constant amount of antibody and radiolabeled antigen, and using known concentrations of unlabeled antigen, a standard (calibration) curve can be plotted showing antigen concentration versus the amount of radiolabeled antigen bound or versus radiolabeled antigen unbound, or versus a ratio of the two measurements. The concentration of antigen in an unknown sample can be read from the standard curve by determining the amount of bound or free radiolabeled antigen (or ratio of the two measurements) resulting when the unknown sample is mixed with the amount of radiolabeled antigen and antibody used to prepare the curve. In all radioimmunoassay procedures it is necessary to provide means for separating the bound from the free labeled tracer material. Many widely varied procedures have been developed and used; exemplary procedures are electrophoresis; chromatography; ion exchange; adsorption to dextran coated charcoal, talc, or cellulose; and a number of solid-phase antibody techniques.

The term "antigen", as used in the field of radioimmunoassays, may cover substances of limited immunogenicity (ability to generate antibodies). In those cases where the substance to be measured is of limited immunogenicity, the substance can be coupled with an immunogenic carrier, usually a protein, to increase its immunogenicity. A substance that is nonimmunogenic, but acquires immunogenicity when linked with a carrier is referred to as a "hapten".

Radioimmunoassay techniques have been used to determine the concentration in body fluids of various endogenous and exogenous steroids. In the development of radioimmunoassays for the various steriods, the preparation of a radiolabeled antigen is of primary concern. Possible radioisotope labels are tritium, carbon-14, iodine-125, iodine-131, and others. However, because tritium and carbon-14 must be counted by liquid scintillation (a time-consuming and expensive process), iodine-125 and iodine-131 are more desirable. For reasons well-recognized in the art (e.g., half-life, radiation hazard, counting efficiency and others) iodine-125 has become the radioisotope of choice for use in steroid radioimmunoassays.

The chemical structure of steroids is such that it is generally not possible to radioiodinate them directly. It is necessary, therefore, to utilize as a precursor of the radiolabeled antigen a derivative of the steroid to be assayed which can be readily iodinated. In choosing or developing such a derivative, the primary concern is the affinity of the derivative for the antibodies of the steroid to be assayed; the affinity of the derivative for the antibodies should, of course, be as close to the affinity of the steroid for the antibodies as possible.

BRIEF DESCRIPTION OF THE INVENTION

Compounds having the formula

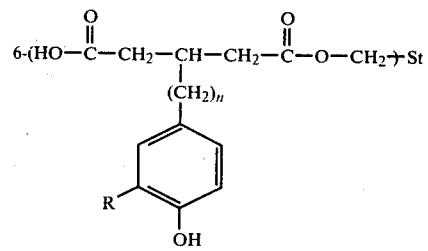

are readily tagged with a radioisotope and can be used (when radiolabeled) as a tracer in radioimmunoassay procedures for the determination of steroid levels in a body fluid. The unlabeled compounds can be coupled with an immunogenic carrier and suitable adjuvant, and injected into animals to induce antibody formation. In formula I, and throughout the specification, R is hydrogen or an alkyl group of 1 to 3 carbon atoms; n is 0, 1, 2, 3 or 4; and St is a 6-dehydro derivative of a 3-oxo-4,5-dehydro steroid intended for radioimmunoassay, said steroid being saturated in the 1,2-position.

Exemplary of 3-oxo-4,5-dehydro steroids intended for radioimmunoassay which can be modified structurally as shown in formula I are cortisol, cortisone, corticosterone, testosterone, 19-nortestosterone and methyltestosterone.

DETAILED DESCRIPTION OF THE INVENTION

The steroids of formula I can be prepared using the corresponding 6-hydrosteroid as the starting material. Many of these starting steroids (St-H) will be 17α,21-dihydroxy pregnenes. In these instances, it will be necessary to protect the substituents in the 17-, 20- and 21-positions prior to running the reactions needed to prepare the steroids of formula I. Various methods for protecting these substituents will be apparent to the practitioner of this invention. An exemplary method comprises the reaction of the unprotected steroid with paraformaldehyde in the presence of hydrochloric acid to yield the corresponding 17,20:20,21-bis-methylenedioxy derivative.

Reaction of the 6-hydrosteroid starting material (protected, if necessary) with formaldehyde in the presence of a secondary amine, e.g., pyrrolidine, affords a mixture of 6α- and 6β-hydroxymethyl steroids having the formula

II these derivatives can be separated using conventional techniques. In formula II, and throughout the specification St′ can be St or the corresponding protected steroid moiety. The above reaction can be carried out in an alcohol solvent, preferably in an inert atmosphere, e.g., nitrogen or argon. The absence of oxygen during the reaction minimizes the formation of significant amounts of 6α- and 6β-hydroxy steroids as by-products.

Alternatively, the 6-hydrosteroid starting material (protected if necessary) can be reacted with pyrrolidine in an alcoholic solvent to yield III 3-[(1-pyrrolidinyl)→St‴-3,4,5,6-dehydro, wherein St‴ is a steroid saturated in the A and B rings. Compounds of this type are known; see, for example, *Helvetica Chimica Acta*, 56(7):2396–2404 (1973). An intermediate of formula III can then be reacted with formaldehyde in an alcoholic solvent to yield the corresponding 6α- and 6β-hydroxymethyl steroids of formula II.

The 6α- and 6β-hydroxymethyl steroids of formula II can be reacted with a glutaric anhydride derivative having the formula

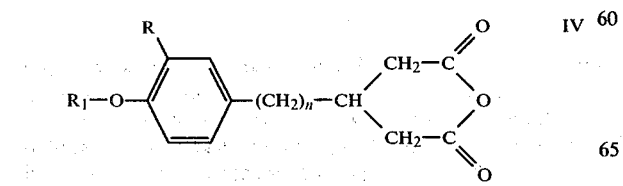

IV to yield the corresponding steroid having the formula

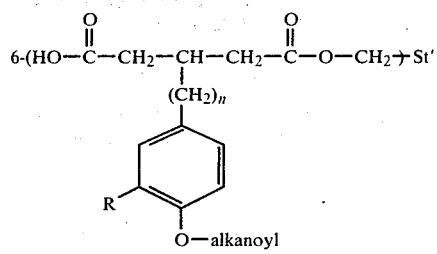

V

The reaction can be run in the presence of an organic base (e.g., a nitrogen containing heterocyclic such as pyridine or a tertiary amine such as triethylamine), preferably at an elevated temperature.

Removal of the phenolic hydroxyl protecting group in a compound of formula V (and, where necessary, removal of the protecting group from the 17β, 20- and 21-positions) yields the corresponding steroid product of formula I.

The anhydrides of formula IV can be prepared by first reacting a 4-methoxyphenyl aldehyde having the formula

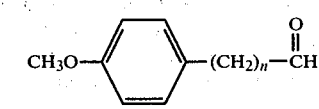

VI with at least 2 molar equivalents of cyanoacetic acid in the presence of a base (e.g., sodium hydroxide) to yield, on acid hydrolysis, a compound having the formula

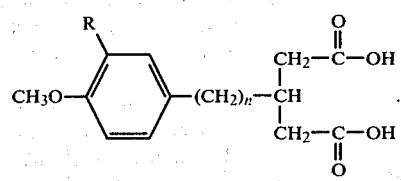

VII

An alternative preparation for the compound of formula VII wherein n is 0 and R is hydrogen, i.e., 3-(4-methoxyphenyl)glutaric acid, is disclosed by Smith et al., *J.A.C.S.*, 72, 1877 (1950). In that procedure, anisaldehyde is condensed with ethyl acetoacetate in the presence of piperidine to give ethyl anisal-bisacetoacetate. Cleavage of this product to give the desired 3-(4-methoxyphenyl)glutaric acid can be accomplished with boiling alcoholic sodium hydroxide solution.

Demethylation of the glutaric acid derivatives of formula VII results in glutaric acid derivatives having the formula

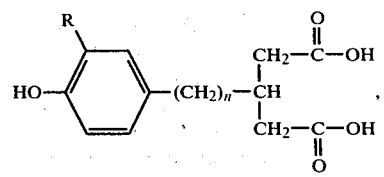

VIII and can be accomplished by following one of the several procedures known in the art for the demethylation of aryl methyl ethers. One such procedure, described by Feutrill et al., *Aust. J. Chem.*, 25, 1719 (1972), involves the treatment of the aryl methyl ether with thioethoxide ion (readily prepared in situ from ethanethiol and sodium hydride) in a polar aprotic solvent, preferably dimethylformamide.

The phenolic hydroxy group of a compound of formula VIII can be protected with an alkanoyl group using art-recognized procedures. One such procedure comprises reacting the glutaric acid derivative with the appropriate acid anhydride (acetic anhydride is preferred). The preferred method of preparing a glutaric anhydride derivative of formula IV from the glutaric acid derivative of formula VIII is to combine the conversion of the acid to anhydride and the protection of the phenolic hydroxy group into a single step. When the $R_1$ protecting group is acetyl, this would involve heating a glutaric acid derivative of formula VIII in acetic anhydride.

The compounds of formula I can be coupled with an immunogenic carrier, such as a high molecular weight protein of which bovine serum albumin and thyroglobulin are exemplary, and if necessary an adjuvant in order to produce a substance capable of inducing antibody formation in animals. Procedures for such couplings are well known in the art; see, for example, Parker, "Radioimmunoassay of Biologically Active Compounds", Prentice-Hall, Inc., New Jersey (1976).

The compounds of formula I can be labeled ("tagged") with a radioisotope, preferably iodine-125 or iodine-131, and most preferably iodine-125, using procedures well known in the art, to yield a radiolabeled hapten having the formula

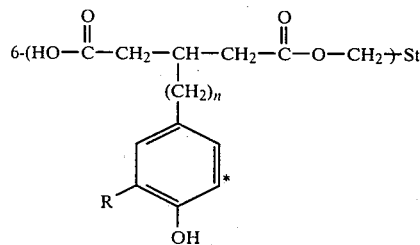

The asterisk (*) in formula IX indicates tagging with a radioisotope. Exemplary of the methods known in the art is the method of Hunter and Greenwood; see *Nature*, 194:495 (1962). The radiolabeled compounds of formula IX form an integral part of this invention.

The radiolabeled compounds of formula IX can be used as tracers in radioimmunoassay procedures following the general principles set forth in the Background of the Invention, supra. Exemplary detailed procedures are described in Jaffe et al., "Methods of Hormone Radioimmunoassay", Academic Press, New York (1974) and Berson et al., "Methods in Investigative and Diagnostic Endocrinology", Vol. 3 on "Steroid Hormones", North Holland, Amsterdam (1975). The radiolabeled compounds of this invention may also be used as reagents in the automated radioimmunoassay system of Brooker et al. disclosed in U.S. Pat. No. 4,022,577, issued May 10, 1977.

The following examples are specific embodiments of this invention.

EXAMPLE 1

(6α,11β)-6-[[DL-4-Carboxy-3-(4-hydroxyphenyl)-1-oxobutoxy]methyl]-11,17,21-trihydroxypregn-4-ene-3,20-dione (cortisol derivative)

(A)

11β-Hydroxy-6-(hydroxymethyl)-17,20:20,21-bis-[methylenebis(oxy)]pregn-4-en-3-one (6α and 6β-isomers)

A suspension of 11β-hydroxy-17,20:20,21-bis[methylenebis(oxy)]pregn-4-en-3-one (1.6 g) in methanol (50 ml) containing pyrrolidine (1.1 g) is refluxed until a homogeneous solution is obtained. The solution is then cooled to room temperature and a 37% formaldehyde solution (5.0 ml) is added. The solution is then refluxed for 15 minutes and the solvents are evaporated to afford 1.7 g of a gummy residue.

The above reaction is repeated two more times on 3.6 g each of the starting steroid. The materials from the three runs are then pooled and chromatographed on a silica gel column to isolate (i) 6.8 g of the starting steroid, (ii) 1.05 g of a mixture of the 6α and 6β-isomers of the title compound, and (iii) 0.8 g of a mixture of the 6α and 6β-isomers of 6,11β-dihydroxy-17,20:20,21-bis[methylenebis(oxy)]pregn-4-en-3-one.

The 6α and 6β-isomers of the 6-hydroxymethyl steroid (1.05 g) are separated by repeated thin-layer chromatography on silica gel plates to afford 0.25 g of the 6α-isomer, melting point 228°–245° C., and 0.74 g of the 6β-isomer, melting point 175°–185° C.

(B)

(6α,11β)-6-[[DL-3-[4-(Acetyloxy)phenyl]-4-carboxy-1-oxobutoxy]methyl]-11-hydroxy-17,20:20,21-bis[methylenebis(oxy)]pregn-4-en-3-one A solution of 105 mg of 11β-hydroxy-6α-(hydroxymethyl)-17,20:20,21-bis[methylenebis(oxy)]pregn-4-en-3-one in 0.8 ml of dry pyridine containing 180 mg of 3-[4-(acetyloxy)phenyl]glutaric anhydride is heated in a bath at 70°–80° C. for 3.0 hours. The pyridine is then evaporated in vacuo, the residue is dissolved in ethyl acetate, washed with 5% hydrochloric acid and water, and evaporated to a residue. This is subjected to thin-layer chromatography on silica gel plates to isolate 113 mg of the title compound, melting point 117°–124° C.

(C)

(6α,11β)-6-[[DL-4-Carboxy-3-(4-hydroxyphenyl)-1-oxobutoxy]methyl]-11-hydroxy-17,20:20,21-bis[methylenbis(oxy)]pregn-4-en-3-one A solution of 110 mg of (6α,11β)-6-[[DL-3-[4-(acetyloxy)phenyl]-4-carboxy-1-oxobutoxy]methyl]-11-hydroxy-17,20:20,21-bis[methylenbis(oxy)]pregn-4-en-3-one in 8 ml of methanol is adjusted to pH 9.0 with triethylamine and refluxed in an oil bath for 22 hours. The mixture is then cooled, acidified with 5% hydrochloric acid, concentrated in vacuo to remove most of the methanol, diluted with water, and extracted with ethyl acetate. The ethyl acetate solution is washed with a saturated sodium chloride solution, dried and evaporated to afford 95 mg of the title compound, melting point 105°–118° C. A thin-layer chromatographic examination shows that this material contains only traces of impurities.

(D)
(6α,11β)-6-[[DL-4-Carboxy-3-(4-hydroxyphenyl)-1-oxobutoxy]methyl]-11,17,21-trihydroxypregn-4-ene-3,20-dione A solution of 60 mg of (6α,11β)-6-[[DL-4-carboxy-3-(4-hydroxyphenyl)-1-oxobutoxy]methyl]-11-hydroxy-17,20:20,21-bis[methylenbis(oxy)]pregn-4-en-3-one in 4 ml of 50% acetic acid is heated at 100° C. for 4.0 hours under nitrogen. The solvents are then evaporated in vacuo and the residue is subjected to preparative thin-layer chromatography on silica gel plates to afford 30 mg of the title compound, melting point 103°–128° C.

EXAMPLE 2

(6β,11β)-6-[[DL-4-Carboxy-3-(4-hydroxyphenyl)-1-oxobutoxy]methyl]-11,17,21-trihydroxypregn-4-ene-3,20-dione

(A)
(6β,11β)-6-[[DL-3-[4-(Acetyloxy)phenyl]-4-carboxy-1-oxobutoxy]methyl]-11-hydroxy-17,20:20,21-bis[methylenebis(oxy)]pregn-4-en-3-one A solution of 11β-hydroxy-6β-(hydroxymethyl)-17,20:20,21-bis[methylenebis(oxy)]pregn-4-en-3-one (300 mg) is reacted with 3-[4-(acetyloxy)phenyl]glutaric anhydride (515 mg) following the procedure described in Example 1B to afford 295 mg of the title compound, melting point 99°–119° C.

(B)
(6β,11β)-6-[[DL-4-Carboxy-3-(4-hydroxyphenyl-1-oxobutoxy]methyl]-11-hydroxy-17,20:20,21-bis[methylenebis(oxy)]pregn-4-en-3-one (6β,11β)-6-[[DL-3-[4-(Acetyloxy)phenyl]-4-carboxy-1-oxobutoxy]methyl]-11-hydroxy-17,20:20,21-bis[methylenebis(oxy)]pregn-4-en-3-one (325 mg) in methanol (18 ml is reacted following the procedure described in Example 1C to afford 305 mg of the title compound, melting point 103°–128° C.

(C)
(6β,11β)-6-[[DL-4-Carboxy-3-(4-hydroxyphenyl)-1-oxobutoxy]methyl]-11,17,21-trihydroxypregn-4-ene-3,20-dione A solution of 100 mg of (6β,11β)-6-[[DL-4-carboxy-3-(4-hydroxyphenyl)-1-oxobutoxy]methyl]-11-hydroxy-17,20:20,21-bis[methylenebis(oxy)]pregn-4-en-3-one is reacted in 4.0 ml of 50% acetic acid following the procedure described in Example 1D to afford 26 mg of the title compound, melting point 177°–205°. Spectral examination shows that this material is contaminated with a small amount of the 6α-isomer.

EXAMPLES 3–9

Following the procedures of Examples 1 and 2, but substituting the starting steroid listed in column I for the cortisol derivative of Example 1A and the anhydride reagent listed in column II for 3-[4-(acetyloxy)phenyl]-glutaric anhydride, yields the α- and β-isomers compound listed in column III. In those instances wherein the starting steroid is not a bis-methylenedioxy derivative, the procedures of Examples 1D and 2C will, of course, not be necessary.

| | Column I | Column II | Column III |
| --- | --- | --- | --- |
| 3 | 17,20:20,21-bis-[methylenebis(oxy)]pregn-4-ene-3,11-dione | 3-[4-(acetyloxy)phenyl]-glutaric anhydride | 6-[[DL-4-carboxy-3-(4-hydroxyphenyl)-1-oxobutoxy]methyl]-17,21-dihydroxypregn-4-ene-3,11,20-trione |
| 4 | 11β,21,dihydroxypregn-4-ene-3,20-dione | 3-[4-(acetyloxy)phenyl]-glutaric anhydride | 6-[[DL-4-carboxy-3-(4-hydroxyphenyl)-1-oxobutoxy]methyl]-11β,21-dihydroxypregn-4-ene-3,20-dione |
| 5 | pregn-4-ene-3,20-dione | 3-[4-(acetyloxy)-3-methylphenyl]glutaric anhydride | 6-[[DL-4-carboxy-3-(4-hydroxy-3-methylphenyl)-1-oxobutoxy]methyl]pregn-4-ene-3,20-dione |
| 6 | 17β-hydroxyandrost-4-en-3-one | 3-[[4-(acetyloxy)phenyl]-methyl]glutaric anhydride | 6-[[DL-4-carboxy-3-[(4-hydroxyphenyl)methyl]-1-oxobutoxy]methyl]-17β-hydroxyandrost-4-en-3-one |
| 7 | 19-nor-17β-hydroxyandrost-4-en-3-one | 3-[2-[4-(acetyloxy)phenyl]-ethyl]glutaric anhydride | 19-nor-6-[[DL-4-carboxy-3-[2-(4-hydroxyphenyl)-ethyl]-1-oxobutoxy]-methyl]-17β-hydroxyandrost-4-en-3-one |
| 8 | 17β-hydroxy-17α-methyl-androst-4-en-3-one | 3-[3-[4-(acetyloxy)phenyl]-propyl]glutaric anhydride | 6[[DL-4-carboxy-3-[3-(4-hydroxyphenyl)propyl]-1-oxobutoxy]methyl]-17β-hydroxy-17α-methyl-androst-4-en-3-one |
| 9 | 11β-hydroxy-17,20:20,21-bis[methylenebis(oxy)]-pregn-4-en-3-one | 3-[4-[4-(acetyloxy)phenyl]-butyl]glutaric anhydride | 6-[[DL-4-carboxy-3-[4-(4-hydroxyphenyl)butyl]-1-oxobutoxy]methyl]-11β,17,21-trihydroxypregn-4-ene-3,20-dione |

What is claimed is:
1. A steroid having the formula

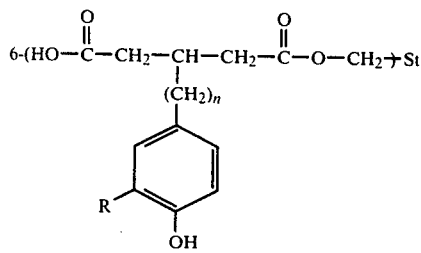

wherein St is a 6-dehydro derivative of a 3-oxo-4,5-dehydro steroid intended for radioimmunoassay, said steriod being saturated in the 1,2-position; R is hydrogen or alkyl of 1 to 3 carbon atoms; and n is 0, 1, 2, 3 or 4.

2. A steroid in accordance with claim 1 wherein R is hydrogen.

3. A steroid in accordance with claim 1 wherein R is alkyl of 1 to 3 carbon atoms.

4. A steroid in accordance with claim 1 wherein n is 0.

5. A steroid in accordance with claim 1 wherein n is 1.

6. A steroid in accordance with claim 1 wherein n is 2.

7. A steroid in accordance with claim 1 wherein n is 3.

8. A steroid in accordance with claim 1 wherein n is 4.

9. The steroid in accordance with claim 1 having the name (6α,11β)-6-[[DL-4-carboxy-3-(4-hydroxyphenyl)-1-oxobutoxy]methyl]-11,17,21-trihydroxypregn-4-ene-3,20-dione.

10. The steroid in accordance with claim 1 having the name (6β,11β)-6-[[DL-4-carboxy-3-(4-hydroxyphenyl)-1-oxobutoxy]methyl]-11,17,21-trihydroxypregn-4-ene-3,20-dione.

11. A steroid having the formula

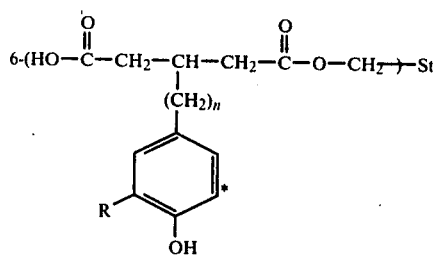

wherein St is a 6-dehydro derivative of a 3-oxo-4,5-dehydro steroid intended for radioimmunoassay, said steroid saturated in the 1,2-position; R is hydrogen or alkyl of 1 to 3 carbon atoms; n is 0, 1, 2, 3 or 4; and the asterisk (*) indicates tagging with iodine-125 or iodine-131.

12. A steroid substituted in the 6-position with a group having the formula

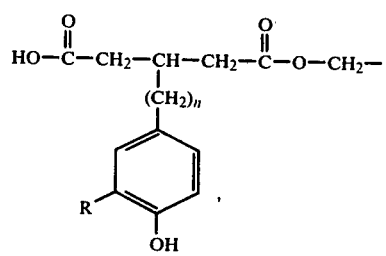

wherein R is hydrogen or alkyl of 1 to 3 carbon atoms and n is 0, 1, 2, 3 or 4, and wherein the steroid is cortisol, cortisone, corticosterone, testosterone, 19-nortestosterone or methyltestosterone.

* * * * *